(12) United States Patent
Gonzalez et al.

(10) Patent No.: US 11,331,220 B2
(45) Date of Patent: May 17, 2022

(54) AUTOMATIC PATIENT POSITIONING WITHIN A LASER EYE SURGERY SYSTEM

(71) Applicant: AMO DEVELOPMENT, LLC, Santa Ana, CA (US)

(72) Inventors: Javier G. Gonzalez, Palo Alto, CA (US); David A. Dewey, Sunnyvale, CA (US); Noah Bareket, Saratoga, CA (US); Michael A. Campos, Fremont, CA (US); Yu-tai Ray Chen, Union City, CA (US); David D. Scott, Oakland, CA (US)

(73) Assignee: AMO Development, LLC, Santa Ana, CA (US)

( * ) Notice: Subject to any disclaimer, the term of this patent is extended or adjusted under 35 U.S.C. 154(b) by 730 days.

(21) Appl. No.: 14/885,824

(22) Filed: Oct. 16, 2015

(65) Prior Publication Data

US 2016/0106581 A1     Apr. 21, 2016

Related U.S. Application Data

(60) Provisional application No. 62/065,178, filed on Oct. 17, 2014.

(51) Int. Cl.
*A61F 9/009*      (2006.01)
*A61B 5/00*      (2006.01)
(Continued)

(52) U.S. Cl.
CPC .............. *A61F 9/009* (2013.01); *A61B 5/704* (2013.01); *A61G 15/02* (2013.01); *A61B 5/6844* (2013.01);
(Continued)

(58) Field of Classification Search
CPC .. A61F 2009/0035; A61F 9/007; A61F 9/008; A61F 2009/00851; A61B 3/102;
(Continued)

(56) References Cited

U.S. PATENT DOCUMENTS 5,459,570 A    10/1995   Swanson et al.
5,720,894 A    2/1998   Neev et al.
(Continued)

FOREIGN PATENT DOCUMENTS

EP       2478830 A2 *   7/2012  ............. A61B 3/102
EP       2478830 A2 *   7/2012  ............. A61B 3/102
(Continued)

OTHER PUBLICATIONS

International Search Report and Written Opinion for Application No. PCT/US2015/056080, dated Dec. 23, 2015, 11 pages.

*Primary Examiner* — Caitlin A Carreiro
(74) *Attorney, Agent, or Firm* — Johnson & Johnson Surgical Vision, Inc.

(57) ABSTRACT

A laser eye surgery system produces a treatment beam that includes a plurality of laser pulses. An optical coherence tomography (OCT) subsystem produces a source beam used to locate one or more structures of an eye. The OCT subsystem is used to sense the distance between a camera objective on the underside of the laser eye surgery system and the patient's eye. Control electronics compare the sensed distance with a pre-determined target distance, and reposition a movable patient support toward or away the camera objective until the sensed distance is at the pre-determined target distance. A subsequent measurement dependent upon the spacing between the camera objective and the patient's eye is performed, such as determining the astigmatic axis by observing the reflection of a plurality of point source LEDs arranged in concentric rings off the eye.

8 Claims, 7 Drawing Sheets

(51) Int. Cl.
*A61G 15/02* (2006.01)
*A61F 9/008* (2006.01)
*A61F 9/007* (2006.01)
*A61F 9/00* (2006.01)

(52) U.S. Cl.
CPC ............... *A61F 9/007* (2013.01); *A61F 9/008* (2013.01); *A61F 2009/0052* (2013.01); *A61F 2009/0087* (2013.01); *A61F 2009/00846* (2013.01); *A61F 2009/00851* (2013.01); *A61F 2009/00887* (2013.01)

(58) Field of Classification Search
CPC ..... A61B 18/20; A61B 5/0066; A61B 90/361; A61B 1/00172; A61B 3/1005; A61B 5/0064; A61B 3/14; G01B 9/0203; G01B 9/02091
USPC ....... 128/845; 606/1, 10, 4–6; 351/205, 208, 351/206; 600/310, 407, 473, 476
See application file for complete search history.

(56) References Cited

U.S. PATENT DOCUMENTS

| | | |
|---|---|---|
| 5,748,352 A | 5/1998 | Hattori |
| 5,748,898 A | 5/1998 | Ueda |
| 5,957,915 A | 9/1999 | Trost |
| 5,984,916 A | 11/1999 | Lai |
| 6,019,472 A | 2/2000 | Koester et al. |
| 6,053,613 A | 4/2000 | Wei et al. |
| 6,111,645 A | 8/2000 | Tearney et al. |
| 6,454,761 B1 | 9/2002 | Freedman |
| 7,655,002 B2 | 2/2010 | Myers et al. |
| 7,717,907 B2 | 5/2010 | Ruiz et al. |
| 8,262,646 B2 | 9/2012 | Frey et al. |
| 8,350,183 B2 | 1/2013 | Vogel et al. |
| 8,382,745 B2 | 2/2013 | Naranjo-Tackman et al. |
| 8,394,084 B2 | 3/2013 | Blumenkranz et al. |
| 8,414,564 B2 | 4/2013 | Goldshleger et al. |
| 8,425,497 B2 | 4/2013 | Blumenkranz et al. |
| 8,500,724 B2 | 8/2013 | Blumenkranz et al. |
| 2003/0231284 A1* | 12/2003 | Lee .............. A61B 3/107 351/212 |
| 2010/0027020 A1* | 2/2010 | Nebosis ............. G01N 21/4795 356/450 |
| 2011/0228218 A1* | 9/2011 | Hauger ............. G01B 9/02004 351/205 |
| 2011/0292341 A1 | 12/2011 | Somani et al. |
| 2011/0319873 A1 | 12/2011 | Raksi et al. |
| 2011/0319875 A1 | 12/2011 | Loesel et al. |
| 2014/0163534 A1* | 6/2014 | Angeley .............. A61F 9/00825 606/4 |
| 2014/0253926 A1* | 9/2014 | Lee ........... A61B 3/102 356/479 |
| 2014/0343541 A1 | 11/2014 | Scott et al. |
| 2015/0018674 A1 | 1/2015 | Scott et al. |

FOREIGN PATENT DOCUMENTS

| | | |
|---|---|---|
| JP | S59137052 A | 8/1984 |
| JP | 2012147976 A | 8/2012 |
| JP | 2014144178 A | 8/2014 |
| WO | 9965431 A1 | 12/1999 |

* cited by examiner

AUTOMATIC PATIENT POSITIONING WITHIN A LASER EYE SURGERY SYSTEM

RELATED APPLICATION

This application is a non-provisional application and claims the benefit under 35 U.S.C. § 119(e) of U.S. Provisional Application Ser. No. 62/065,178, filed Oct. 17, 2014, which is incorporated herein in its entirety as if fully set forth.

FIELD OF THE INVENTION

The present application pertains to systems and methods for automatically positioning a patient relative to a laser-assisted eye surgery system.

BACKGROUND

A cataract is formed by opacification of the crystalline lens or its envelope—the lens capsule—of the eye. The cataract obstructs passage of light through the lens. A cataract can vary in degree from slight to complete opacity. Early in the development of an age-related cataract, the power of the lens may be increased, causing near-sightedness (myopia). Gradual yellowing and opacification of the lens may reduce the perception of blue colors as those wavelengths are absorbed and scattered within the crystalline lens. Cataract formation typically progresses slowly resulting in progressive vision loss. If left untreated, cataracts may cause blindness.

A common cataract treatment involves replacing the opaque crystalline lens with an artificial intraocular lens (IOL). Every year, an estimated 15 million cataract surgeries are performed worldwide. Traditionally, cataract surgery has been typically performed using a technique called phacoemulsification in which an ultrasonic tip with associated irrigation and aspiration ports is used to sculpt the relatively hard nucleus of the lens to facilitate removal through an opening made in the anterior lens capsule. Access to the lens nucleus can be provided by performing an anterior capsulotomy in which a small round hole is formed in the anterior side of the lens capsule using a surgical. Access to the lens nucleus can also be provided by performing a manual continuous curvilinear capsulorhexis (CCC) procedure. After removal of the lens nucleus, a synthetic foldable intraocular lens (IOL) can be inserted into the remaining lens capsule of the eye.

One of the most technically challenging and critical steps in the cataract extraction procedure is providing access to the lens nucleus for removal of the cataract by phacoemulsification. The desired outcome is to provide a smooth continuous circular opening through which phacoemulsification of the nucleus can be performed safely and easily, and also through which an intraocular lens may be easily inserted. Because of the criticality of this step, some surgeons prefer a surgical laser beam over manual tools like microkeratomes and forceps since the laser beam can be focused precisely on extremely small amounts of eye tissue, thereby enhancing the accuracy and reliability of the capsulotomy procedure.

Many cataract patients also have refractive visual errors such as astigmatism. Astigmatism can occur when the corneal curvature is unequal. A toric IOL can be used to correct astigmatism, but requires precise rotational and central placement. Additionally, IOLs are not typically used for correction beyond 5D of astigmatism. Many patients, however, have astigmatic visual errors exceeding 5D. For these patients, higher correction beyond 5D typically requires reshaping the cornea to make it more spherical. There are numerous existing approaches for reshaping the cornea, including Corneaplasty, Astigmatic Keratotomy, Corneal Relaxing Incision (CRI), and Limbal Relaxing Incision (LRI). In Astigmatic Keratotomy, Corneal Relaxing Incision (CRI), and Limbal Relaxing Incision (LRI), corneal incisions are made in at a depth in a well-defined manner, allowing the cornea to change shape and become more spherical.

Several commercial laser-assisted eye surgery systems are available to facilitate cataract removal and astigmatism correction. The CATALYS Precision Laser System from Abbott Medical Optics is indicated for anterior capsulotomy, phacofragmentation, and the creation of single plane and multi-plane arc cuts/incisions in the cornea to correct astigmatism. The CATALYS System uses a two-piece liquid-filled interface that docks with the patient's eye and provides a clear optical path for real-time video, OCT imaging, and laser treatment. Aspects of the CATALYS System are disclosed in U.S. Pat. Nos. 8,394,084, 8,500,724, 8,425,497, U.S. Patent Publication 2014/0163534, U.S. patent application Ser. No. 14/256,307, filed Apr. 18, 2014 (published as U.S. Patent Publication No. US 2015/0018674 on Jan. 15, 2015), and U.S. patent application Ser. No. 14/255,430, filed Apr. 17, 2014 (published as U.S. Patent Publication No. 2014/0343541 on Nov. 20, 2014), the contents of all of which are incorporated herein by reference as if fully set forth. Other systems for laser cataract surgery are the LenSx Laser from Alcon Laboratories, Inc., the LENSAR Laser System from LENSAR, Inc., and the VICTUS Femtosecond Laser Platform from TECHNOLAS Perfect Vision GmbH a Bausch+Lomb Company.

One drawback with current systems is the time spent on, and ancillary equipment required for, determining the astigmatic axis of the patient's eye relative to the laser system. In conventional keratometry using topography principles, the astigmatic axis of a patient's eye is determined by analyzing reflections off the eye from circles of light typically generated by circular patterns of LEDs. The accuracy of this method depends on a number of factors that affect measurements used in assessing the astigmatic power and axis. Consequently, improved methods and systems for positioning the patient and determining the astigmatic power and axis of a patient's eye during preparation for a laser-assisted surgery are needed.

SUMMARY

Hence, to obviate one or more problems due to limitations and disadvantages of the related art, one object of this disclosure provides improved laser eye surgery systems, and related methods. The laser eye surgery systems use a laser to form precise incisions in the cornea, in the lens capsule, and/or in the crystalline lens nucleus. In a preferred embodiment, a laser eye surgery system includes a laser cutting subsystem to produce a laser pulse treatment beam to incise tissue within the eye. It further includes an optical coherence tomography (OCT) scanning subsystem to measure the spatial disposition of external and internal structures of the eye in which incisions can be formed. The laser eye surgery system further includes an alignment subsystem, shared optics operable to scan the treatment beam, and an alignment subsystem relative to the laser eye surgery system. The alignment subsystem can include a video subsystem that can be used to, for example, provide images of the eye during docking of the eye to the laser eye surgery system. In a preferred embodiment, a liquid interface is used between a patient interface lens and the eye. The use of the liquid interface avoids imparting undesirable forces to the patient's eye, thereby reducing patient discomfort and folds in the cornea. The alignment and OCT subsystems may be used to detect structures involved with the patient interface.

The present application provides a number of techniques for automatically positioning the patient's eye with respect to the various subsystems in the overall laser eye surgery system. Preferably, the various subsystems are located within a single unit under which the patient's position in a prone position looking up. The patient lies on a horizontal patient support chair that has a mechanical positioning subsystem built into it controlled by the same electronics which control the various subsystems.

A first exemplary technique for automatically positioning the patient utilizes a closed-loop iterative method using the OCT subsystem to determine the Z-axis distance from an objective camera lens to the eye. The method involves using the OCT scanner to measure the distance between the lens and the eye, adjusting the vertical position of the patient support chair, and then re-measuring the distance between the lens and the eye. This sequence continues until an optimum distance between the lens and the eye is reached, depending on several metrics. For example, an optimum distance between the lens and the eye occurs when the reflection from a pattern of circular light dots on the eye is in focus or in extremely sharp contrast. The optimal distance from the camera objective to the cornea that maximizes the contrast of the reflection may be pre-determined by a theoretical analysis of the optical system.

In one embodiment, the laser eye surgery system incorporates an optical coherence tomography (OCT) subsystem that is used to sense the distance between a camera objective on the underside of the laser eye surgery system and the patient's eye. Control electronics compare the sensed distance with a pre-determined target distance, and reposition a movable patient support toward or away the camera objective until the sensed distance is at the pre-determined target distance. A subsequent measurement dependent upon the spacing between the camera objective and the patient's eye is performed, such as determining the astigmatic axis by observing the reflection of a plurality of point source LEDs, or dots, arranged in concentric rings off the eye.

The second technique also uses a closed-loop iteration in which the visible contrast from the reflection of a series of LEDs off the eye is measured and maximized. For instance, a series of light circles comprising individual LEDs may be shone onto the eye and the reflections observed to determine the astigmatic axis of the eye. The automatic positioning technique involves moving the patient support chair in a first direction until the contrast of the reflected LEDs is maximized. The contrast can be maximized by subtraction of adjacent pixels or by averaging power of the midrange frequencies of the 2d Fourier after an annular mask is applied.

A still further method of automatically positioning the patient relative to the laser eye system utilizes a phase detection subsystem to determine when the image of LED dots is in focus. When the split reflections in the face detector are co-registered, the image, and therefore chair position, is optimized. If not, the chair moves to co-register the split reflections.

Finally, another method for automatically positioning a patient uses a light field measurement to gather the reflected image and then a processor calculates the distance at which the reflected rays would have to originate for the image to be in focus. This distance can then be used to drive the chair to the correct height.

This summary and the following detailed description are merely exemplary, illustrative, and explanatory, and are not intended to limit, but to provide further explanation of the invention as claimed. Additional features and advantages of the invention will be set forth in the descriptions that follow, and in part will be apparent from the description, or may be learned by practice of the invention. The objectives and other advantages of the invention will be realized and attained by the structure particularly pointed out in the written description, claims and the appended drawings.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

Methods and systems related to laser eye surgery are disclosed. A laser is used to form precise incisions in the cornea, in the lens capsule, and/or in the crystalline lens nucleus. In a preferred embodiment, a laser eye surgery system includes a laser cutting subsystem to produce a laser pulse treatment beam to incise tissue within the eye, a ranging subsystem to measure the spatial disposition of external and internal structures of the eye in which incisions can be formed, an alignment subsystem, and shared optics operable to scan the treatment beam, a ranging subsystem beam, and/or an alignment beam relative to the laser eye surgery system. The alignment subsystem can include a video subsystem that can be used to, for example, provide images of the eye during docking of the eye to the laser eye surgery system and also provide images of the eye once the docking process is complete. In a preferred embodiment, a liquid interface is used between a patient interface lens and the eye. The use of the liquid interface avoids imparting undesirable forces to the patient's eye.

The present application pertains to systems and methods for automatically positioning a patient relative to a laser-assisted eye surgery system. The positioning techniques described herein can be utilized for a number of purposes, including quickly establishing a preferred distance between the patient's eye and a camera while determining the astigmatic axis. Another use is to rapidly locate the patient's eye when measuring the power or curvature of the cornea. A number of different techniques are described herein, each of which can be used with various laser-assisted ophthalmic surgical systems, such as the commercial systems described in the background discussion. A preferred such commercial system is the CATALYS Precision Laser System from Abbott Medical Optics. Prior to a detailed description of the preferred auto-positioning techniques, the main components of laser-assisted ophthalmic surgical systems will be introduced.

Laser System Configuration

Figure 1:
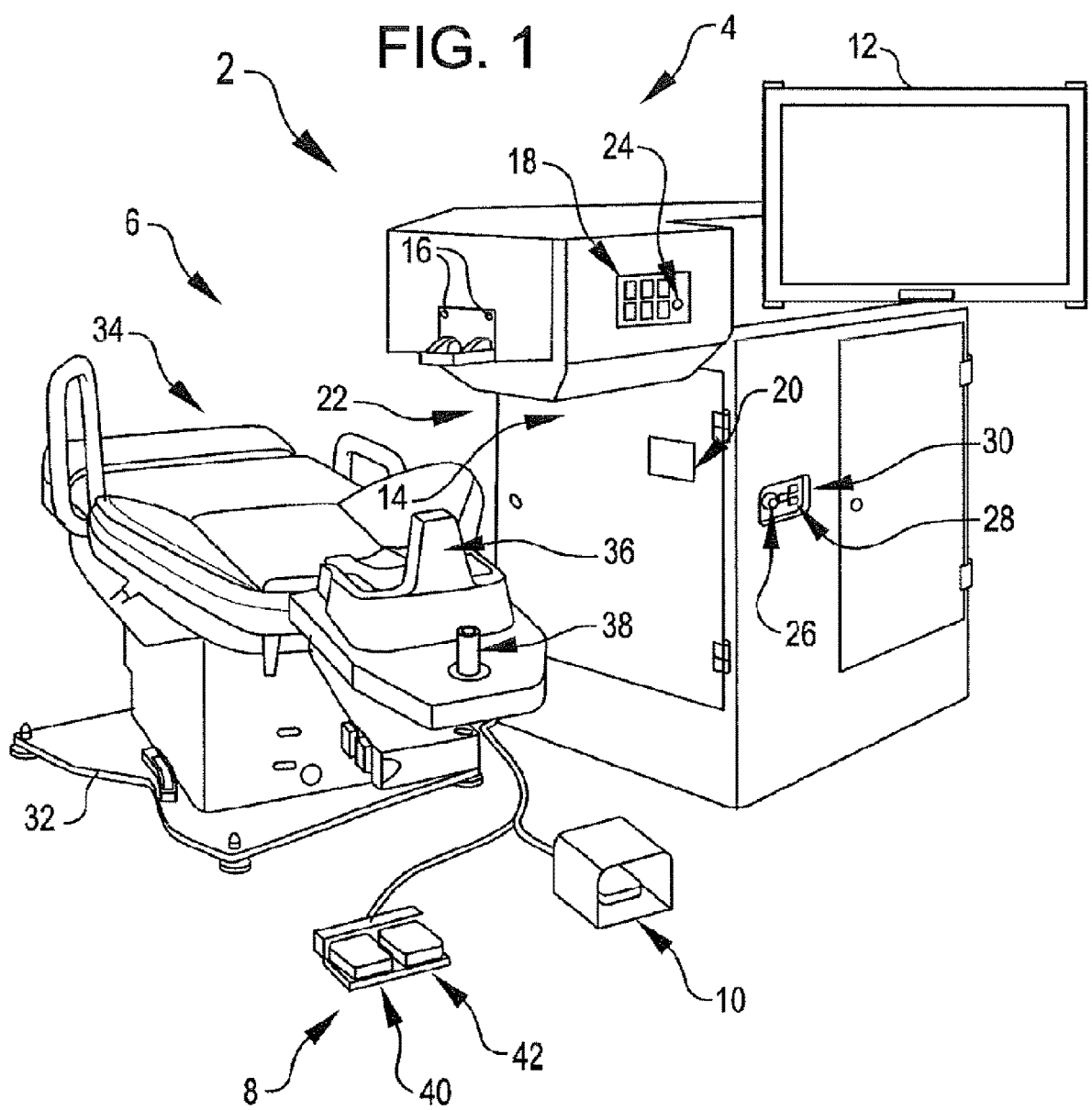
FIG. 1 is a perspective view showing a laser eye surgery system, in accordance with the present application.

FIG. 1 shows a laser eye surgery system 2, in accordance with the present application, operable to form precise incisions in the cornea, in the lens capsule, and/or in the crystalline lens nucleus. The system 2 includes a diagnostic and interventional unit 4, a patient chair 6, a dual function footswitch 8, and a laser footswitch 10.

The diagnostic and interventional unit 4 houses many primary subsystems of the system 2. For example, externally visible subsystems include a touch-screen control panel 12, a patient interface assembly 14, patient interface vacuum connections 16, a docking control keypad 18, a patient interface radio frequency identification (RFID) reader 20, external connections 22 (e.g., network, video output, footswitch, USB port, door interlock, and AC power), laser emission indicator 24, emergency laser stop button 26, key switch 28, and USB data ports 30.

The patient chair 6 includes a base 32, a patient support bed 34, a headrest 36, a positioning mechanism (internal, not shown), and a patient chair joystick control 38 disposed on the headrest 36. The positioning control mechanism is coupled between the base 32 and the patient support bed 34 and headrest 36. The patient chair 6 is configured to be adjusted and oriented in three axes (x, y, and z) using the patient chair joystick control 38. The headrest 36 and a restrain system (not shown, e.g., a restraint strap engaging the patient's forehead) stabilize the patient's head during the procedure. The headrest 36 includes an adjustable neck support to provide patient comfort and to reduce patient head movement. The headrest 36 is configured to be vertically adjustable to enable adjustment of the patient head position to provide patient comfort and to accommodate variation in patient head size.

The patient chair 6 allows for tilt articulation of the patient's legs, torso, and head using manual adjustments. The patient chair 6 accommodates a patient load position, a suction ring capture position, and a patient treat position. In the patient load position, the chair 6 is rotated out from under the diagnostic and interventional unit 4 with the patient chair back in an upright position and patient footrest in a lowered position. In the suction ring capture position, the chair is rotated out from under the diagnostic and interventional unit 4 with the patient chair back in reclined position and patient footrest in raised position. In the patient treat position, the chair is rotated under the diagnostic and interventional unit 4 with the patient chair back in reclined position and patient footrest in raised position.

The patient chair 6 is equipped with a "chair enable" feature to protect against unintended chair motion. The patient chair joystick 38 can be enabled in either of two ways. First, the patient chair joystick 38 incorporates a "chair enable" button located on the top of the joystick. Control of the position of the patient chair 6 via the joystick 38 can be enabled by continuously pressing the "chair enable" button. Alternately, the left foot switch 40 of the dual function footswitch 8 can be continuously depressed to enable positional control of the patient chair 6 via the joystick 38.

In a preferred embodiment, the patient control joystick 38 is a proportional controller. For example, moving the joystick a small amount can be used to cause the chair to move slowly. Moving the joystick a large amount can be used to cause the chair to move faster. Holding the joystick at its maximum travel limit can be used to cause the chair to move at the maximum chair speed. The available chair speed can be reduced as the patient approaches the patient interface assembly 14.

The emergency stop button 26 can be pushed to stop emission of all laser output, release vacuum that couples the patient to the system 2, and disable the patient chair 6. The stop button 26 is located on the system front panel, next to the key switch 28.

The key switch 28 can be used to enable the system 2. When in a standby position, the key can be removed and the system is disabled. When in a ready position, the key enables power to the system 2.

The dual function footswitch 8 is a dual footswitch assembly that includes the left foot switch 40 and a right foot switch 42. The left foot switch 40 is the "chair enable" footswitch. The right footswitch 42 is a "vacuum ON" footswitch that enables vacuum to secure a liquid optics interface suction ring to the patient's eye. The laser footswitch 10 is a shrouded footswitch that activates the treatment laser when depressed while the system is enabled.

In a preferred embodiment, the system 2 includes external communication connections. For example, the system 2 can include a network connection (e.g., an RJ45 network connection) for connecting the system 2 to a network. The network connection can be used to enable network printing of treatment reports, remote access to view system performance logs, and remote access to perform system diagnostics. The system 2 can include a video output port (e.g., HDMI) that can be used to output video of treatments performed by the system 2. The output video can be displayed on an external monitor for, for example, viewing by family members and/or training. The output video can also be recorded for, for example, archival purposes. The system 2 can include one or more data output ports (e.g., USB) to, for example, enable export of treatment reports to a data storage device. The treatments reports stored on the data storage device can then be accessed at a later time for any suitable purpose such as, for example, printing from an external computer in the case where the user without access to network based printing.

Figure 2:
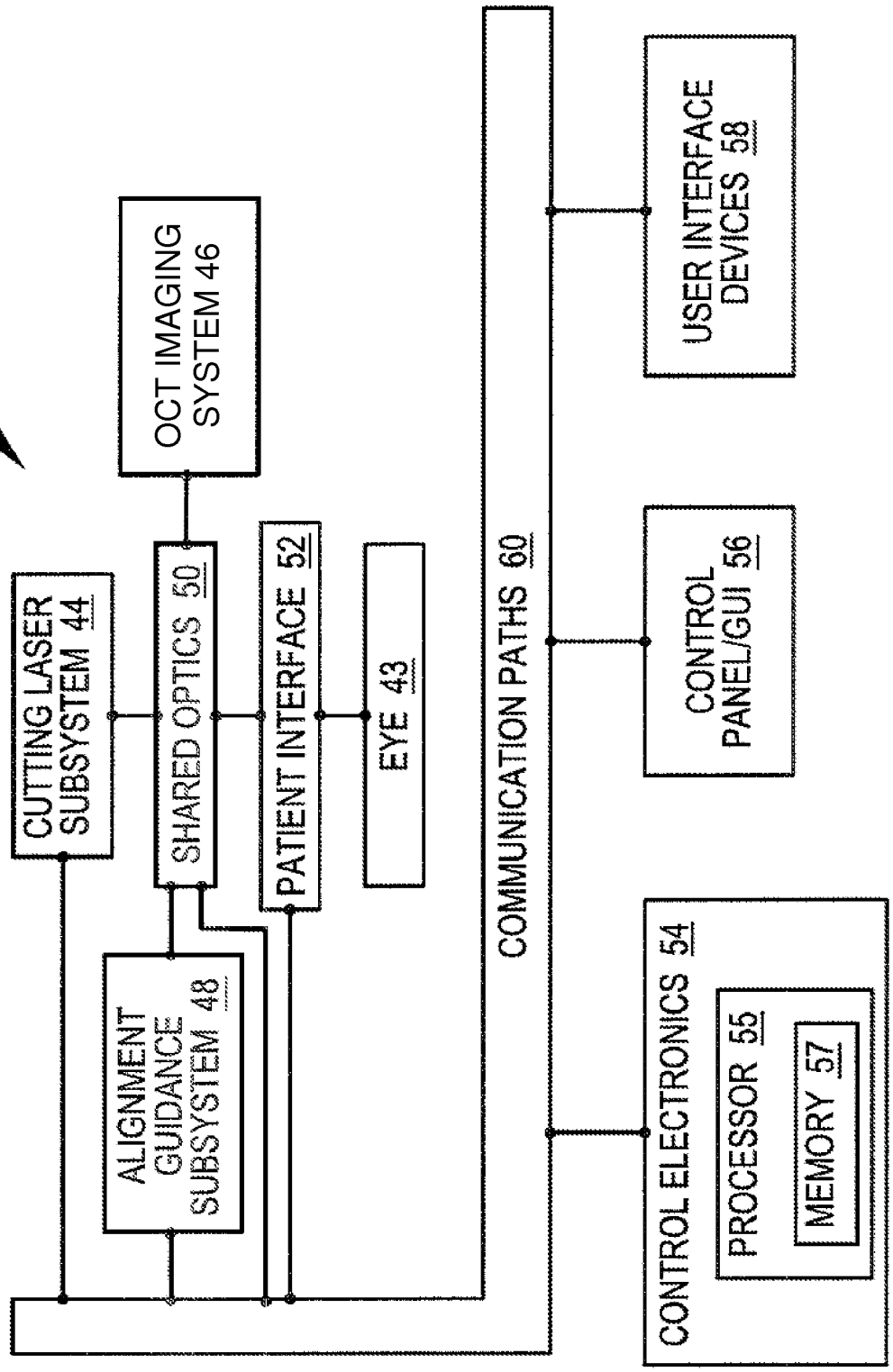
FIG. 2 is a simplified block diagram showing a top level view of the configuration of a laser eye surgery system, in accordance with the present application.

FIG. 2 shows a simplified block diagram of the system 2 coupled with a patient eye 43. The patient eye 43 comprises a cornea, a lens, and an iris. The iris defines a pupil of the eye 43 that may be used for alignment of eye 43 with system 2. The system 2 includes a cutting laser subsystem 44, a OCT imaging system 46, an alignment guidance system 48, shared optics 50, a patient interface 52, control electronics 54, a control panel/GUI 56, user interface devices 58, and communication paths 60. The control electronics 54 are operatively coupled via the communication paths 60 with the cutting laser subsystem 44, the OCT imaging system 46, the alignment guidance subsystem 48, the shared optics 50, the patient interface 52, the control panel/GUI 56, and the user interface devices 58.

In a preferred embodiment, the cutting laser subsystem 44 incorporates femtosecond (FS) laser technology. By using femtosecond laser technology, a short duration (e.g., approximately $10^{-13}$ seconds in duration) laser pulse (with energy level in the micro joule range) can be delivered to a tightly focused point to disrupt tissue, thereby substantially lowering the energy level required as compared to the level required for ultrasound fragmentation of the lens nucleus and as compared to laser pulses having longer durations.

The cutting laser subsystem 44 can produce laser pulses having a wavelength suitable to the configuration of the system 2. As a non-limiting example, the system 2 can be configured to use a cutting laser subsystem 44 that produces laser pulses having a wavelength from 1020 nm to 1050 nm. For example, the cutting laser subsystem 44 can have a diode-pumped solid-state configuration with a 1030 (+/−5) nm center wavelength.

The cutting laser subsystem 44 can include control and conditioning components. For example, such control components can include components such as a beam attenuator to control the energy of the laser pulse and the average power of the pulse train, a fixed aperture to control the cross-sectional spatial extent of the beam containing the laser pulses, one or more power monitors to monitor the flux and repetition rate of the beam train and therefore the energy of the laser pulses, and a shutter to allow/block transmission of the laser pulses. Such conditioning components can include an adjustable zoom assembly to adapt the beam containing the laser pulses to the characteristics of the system 2 and a fixed optical relay to transfer the laser pulses over a distance while accommodating laser pulse beam positional and/or directional variability, thereby providing increased tolerance for component variation.

The OCT imaging system 46 is configured to measure the spatial disposition of eye structures in three dimensions. The measured eye structures can include the anterior and posterior surfaces of the cornea, the anterior and posterior portions of the lens capsule, the iris, and the limbus. In a preferred embodiment, the OCT imaging system 46 utilizes optical coherence tomography (OCT) imaging. As a non-limiting example, the system 2 can be configured to use an OCT imaging system employing wavelengths from 780 nm to 970 nm. For example, the OCT imaging system 46 can include an OCT imaging system that employs a broad spectrum of wavelengths from 810 nm to 850 nm. Such an OCT imaging system can employ a reference path length that is adjustable to adjust the effective depth in the eye of the OCT measurement, thereby allowing the measurement of system components including features of the patient interface that lie anterior to the cornea of the eye and structures of the eye that range in depth from the anterior surface of the cornea to the posterior portion of the lens capsule and beyond.

There are many suitable possibilities for the configuration of the OCT imaging system. For example, alternative suitable configurations include time and frequency domain approaches, single and dual beam methods, swept source, etc., such as those described in U.S. Pat. Nos. 5,748,898; 5,748,352; 5,459,570; 6,111,645; and 6,053,613.

The alignment guidance subsystem 48 can include a laser diode or gas laser that produces a laser beam used to align optical components of the system 2. The alignment guidance subsystem 48 can include LEDs or lasers that produce a fixation light to assist in aligning and stabilizing the patient's eye during docking and treatment. The alignment guidance subsystem 48 can include a laser or LED light source and a detector to monitor the alignment and stability of the actuators used to position the beam in X, Y, and Z. The alignment guidance subsystem 48 can include a video system that can be used to provide imaging of the patient's eye to facilitate docking of the patient's eye 43 to the patient interface 52. The imaging system provided by the video system can also be used to direct via the GUI the location of cuts. The imaging provided by the video system can additionally be used during the laser eye surgery procedure to monitor the progress of the procedure, to track movements of the patient's eye 43 during the procedure, and to measure the location and size of structures of the eye such as the pupil and/or limbus.

The shared optics 50 provides a common propagation path that is disposed between the patient interface 52 and each of the cutting laser subsystem 44, the OCT imaging system 46, and the alignment guidance subsystem 48. In a preferred embodiment, the shared optics 50 includes beam combiners to receive the emission from the respective subsystem (e.g., the cutting laser subsystem 44, and the alignment guidance subsystem 48) and redirect the emission along the common propagation path to the patient interface. In a preferred embodiment, the shared optics 50 includes an objective lens assembly that focuses each laser pulse into a focal point. In a preferred embodiment, the shared optics 50 includes scanning mechanisms operable to scan the respective emission in three dimensions. For example, the shared optics can include an XY-scan mechanism(s) and a Z-scan mechanism. The XY-scan mechanism(s) can be used to scan the respective emission in two dimensions transverse to the propagation direction of the respective emission. The Z-scan mechanism can be used to vary the depth of the focal point within the eye 43. In a preferred embodiment, the scanning mechanisms are disposed between the laser diode and the objective lens such that the scanning mechanisms are used to scan the alignment laser beam produced by the laser diode. In contrast, In a preferred embodiment, the video system is disposed between the scanning mechanisms and the objective lens such that the scanning mechanisms do not affect the image obtained by the video system.

The patient interface 52 is used to restrain the position of the patient's eye 43 relative to the system 2. In a preferred embodiment, the patient interface 52 employs a suction ring that is vacuum attached to the patient's eye 43. The suction ring is then coupled with the patient interface 52, for example, using vacuum to secure the suction ring to the patient interface 52. In a preferred embodiment, the patient interface 52 includes an optically transmissive structure (lens) having a posterior surface that is displaced vertically from the anterior surface of the patient's cornea and a region of a suitable liquid (e.g., a sterile buffered saline solution (BSS)) is disposed between and in contact with the posterior surface and the patient's cornea and forms part of a transmission path between the shared optics 50 and the patient's eye 43. The optically transmissive structure may comprise a lens 84 (see FIG. 3) having one or more curved surfaces. Alternatively, the patient interface 52 may comprise an optically transmissive structure having one or more substantially flat surfaces such as a parallel plate or wedge. In a preferred embodiment, the patient interface lens is disposable and can be replaced at any suitable interval, such as before each eye treatment.

The control electronics 54 controls the operation of and can receive input from the cutting laser subsystem 44, the OCT imaging system 46, the alignment guidance subsystem 48, the patient interface 52, the control panel/GUI 56, and the user interface devices 58 via the communication paths 60. The communication paths 60 can be implemented in any suitable configuration, including any suitable shared or dedicated communication paths between the control electronics 54 and the respective system components.

The control electronics 54 can include any suitable components, such as one or more processor, one or more field-programmable gate array (FPGA), and one or more memory storage devices. In a preferred embodiment, the control electronics 54 controls the control panel/GUI 56 to provide for pre-procedure planning according to user specified treatment parameters as well as to provide user control over the laser eye surgery procedure.

The control electronics 54 may comprise a processor/controller 55 (referred to herein as a processor) that is used to perform calculations related to system operation and provide control signals to the various system elements. A computer readable medium 57 (also referred to as a database or a memory) is coupled to the processor 55 in order to store data used by the processor and other system elements. The processor 55 interacts with the other components of the system as described more fully throughout the present specification. In an embodiment, the memory 57 can include a look up table that can be utilized to control one or more components of the laser system as described herein.

The processor 55 can be a general purpose microprocessor configured to execute instructions and data, such as a Pentium processor manufactured by the Intel Corporation of Santa Clara, Calif. It can also be an Application Specific Integrated Circuit (ASIC) that embodies at least part of the instructions for performing the method in accordance with the embodiments of the present disclosure in software, firmware and/or hardware. As an example, such processors include dedicated circuitry, ASICs, combinatorial logic, other programmable processors, combinations thereof, and the like.

The memory 57 can be local or distributed as appropriate to the particular application. Memory 57 may include a number of memories including a main random access memory (RAM) for storage of instructions and data during program execution and a read only memory (ROM) in which fixed instructions are stored. Thus, memory 57 provides persistent (non-volatile) storage for program and data files, and may include a hard disk drive, flash memory, a floppy disk drive along with associated removable media, a Compact Disk Read Only Memory (CD-ROM) drive, an optical drive, removable media cartridges, and other like storage media.

The user interface devices 58 can include any suitable user input device suitable to provide user input to the control electronics 54. For example, the user interface devices 58 can include devices such as, for example, the dual function footswitch 8, the laser footswitch 10, the docking control keypad 18, the patient interface radio frequency identification (RFID) reader 20, the emergency laser stop button 26, the key switch 28, and the patient chair joystick control 38.

Figure 3:
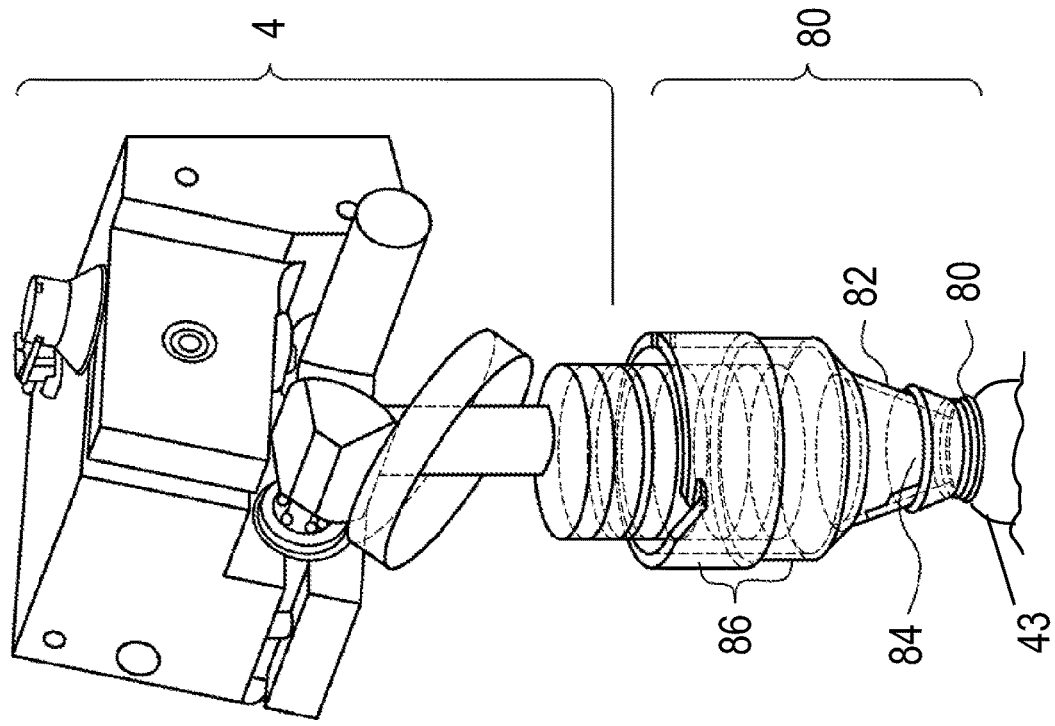
FIG. 3 is a patient interface mechanically coupled with an overhead with a diagnostic and interventional system.

Referring to FIG. 3, one embodiment of a patient interface 52 is shown interfaced with a diagnostic and interventional unit 4 such as that described in reference to FIG. 1, the patient interface 52 comprising an interfacial seal configuration 80 in contact with the eye 43, a conical lower housing portion 82 which houses a focusing lens 84, and a cylindrical upper housing portion 86 with a proximal aspect configured to mechanically interface and couple with the diagnostic and interventional unit 4. Preferably, in the depicted embodiment and other illustrative embodiments that follow, the patient interface 52 is coupled to the diagnostic and interventional unit 4 with a load sensing interface, such as a platform comprising one or more load cells or load sensors (such as MEMS load sensors available from Honeywell, Inc.) configured to provide the operator with output signals or feedback regarding loads being applied at such interface due to coupling with the eye of the patient (i.e., such loads may be monitored since they are representative of contact loads applied to the eye of the patient by the patient interface assembly 52. This feedback may be presented to the user on the control panel/GUI 56 (FIG. 2) for use in adjusting the directionality of positioning control mechanism between the base 32 and the patient support bed 34 and headrest 36 (FIG. 1) during patient coupling to the system.

Figure 4:
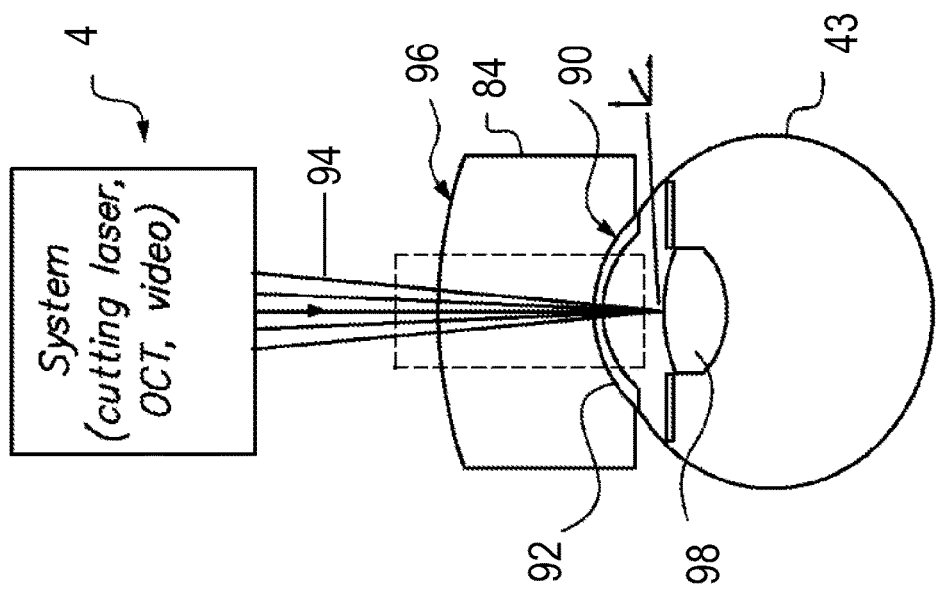
FIG. 4 depicts one embodiment of a focusing lens placed into direct contact with the cornea and/or sclera of the eye and through which system optics view and act on the eye.

FIG. 4 depicts one embodiment of a focusing lens 84 configuration wherein a distal aspect 90 of the lens 84 is placed into direct contact with the cornea and/or sclera 92 of the eye 43. The scanned beam 94 of the cutting laser subsystem 44 exits the unit 4 crosses the proximal surface 96 of the lens 84, passes through the lens, exits across the distal surface 90, crosses the cornea and/or sclera 92, and eventually reaches the crystalline lens 98 to facilitate interventional steps such as capsulorhexis.

Automatic Patient Positioning

It should be understood that the preceding discussion of an exemplary laser assisted eye surgery system provides the context in which the present application is useful. For instance, the automatic positioning techniques described herein may be used to more accurately and quickly determine the astigmatic axis of the patient. Consequently, the subsequent steps of using the cutting laser subsystem 44 via the patient interface assembly 52 are done with the knowledge of the location of the astigmatic axis. The present automatic positioning techniques are accomplished prior to engaging the patient interface assembly 52, as shown, and require no additional equipment from what is already used for the laser surgery steps. Moreover, it is believed that the automatic positioning techniques are more accurate than those used previously, and therefore the location of the astigmatic axis is more accurate, leading to better outcomes.

Figure 5:
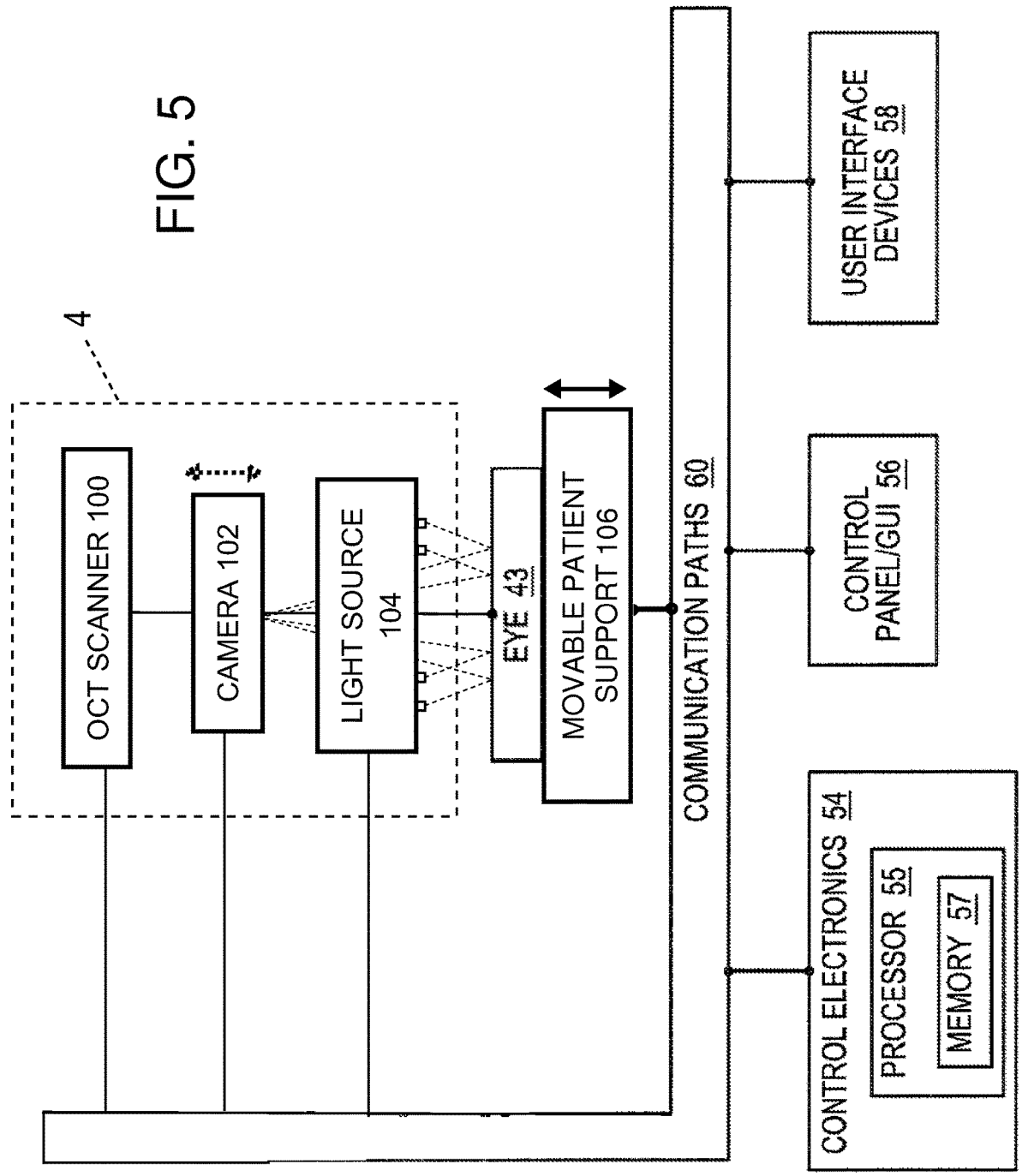
FIG. 5 is a simplified block diagram showing a top level view of the configuration of an automatic patient position system for determining the astigmatic axis incorporated into the laser eye surgery system of the present application.

FIG. 5 is a simplified block diagram showing a top level view of the configuration of an automatic patient position system for setting the patient position (and then determining the astigmatic axis) incorporated into the laser eye surgery system of the present application. The aforementioned diagnostic and interventional unit 4 is shown housing the OCT scanner 100, a camera 102 which may be a video camera, and a light source 104 having a plurality of concentric circles of point source LEDs, or dots, which shine downward toward the eye 43 of the patient. As mentioned previously, the patient resides upon a patient support bed 34 having a headrest 36 and an internal positioning mechanism (FIG. 1), which are here symbolically represented by a movable patient support 106. A double-headed vertical arrow next to the patient support 106 indicates it may be automatically vertically adjusted, but it should also be understood it may be capable of horizontal adjustment. Further, a dashed-line double-headed vertical arrow next to the camera 102 is intended to indicate that it may be moved relative to a stationary patient support 106 in the alternative to establish the desired spacing. Each of these subsystems or components are in communication with the control electronics 54 of the system, and are instructed and monitored by the control panel 56 and user interface devices 58.

Figure 6:
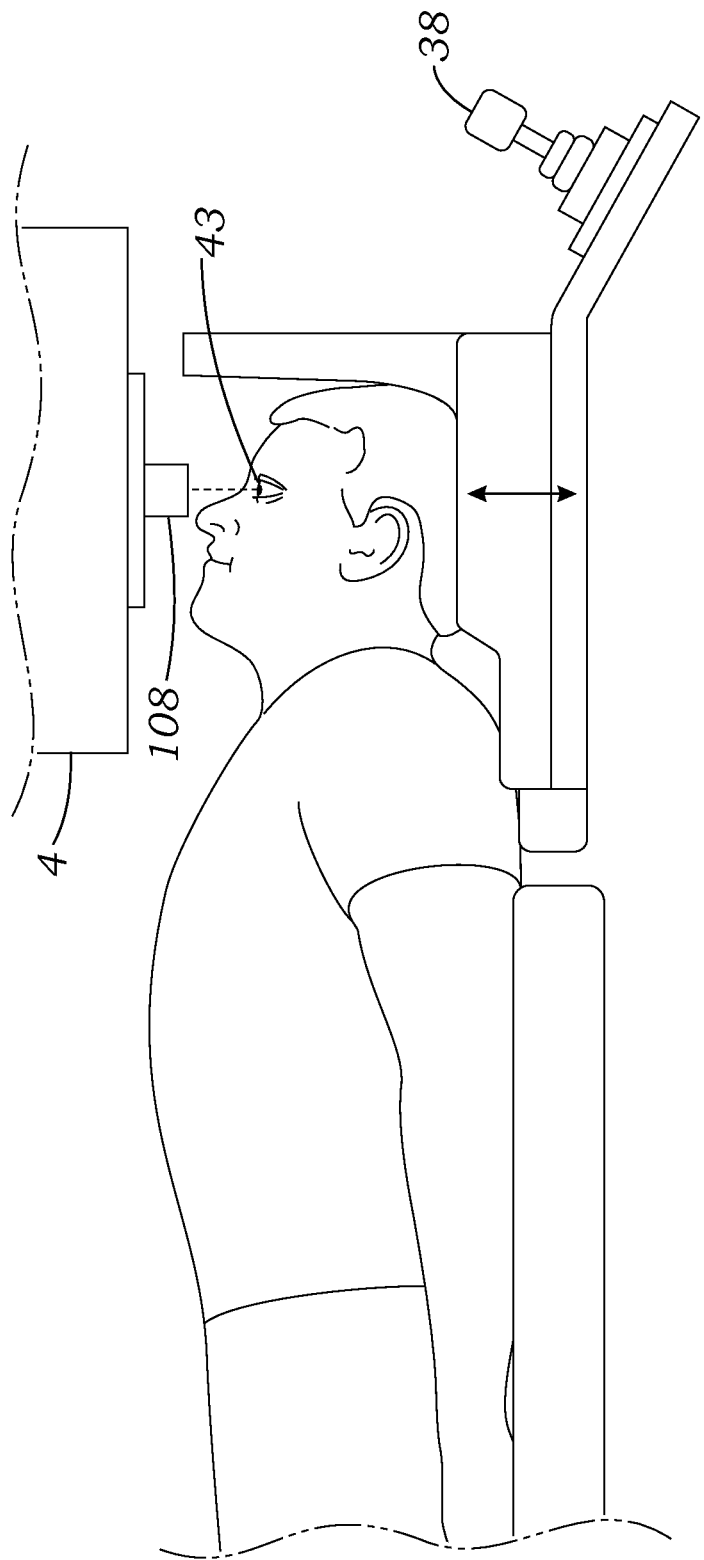
FIG. 6 is a side view of a patient positioned under the diagnostic and interventional system during determination of the astigmatic axis.

FIG. 6 is a side view of a patient positioned under the diagnostic and interventional system 4 during determination of the astigmatic axis. The OCT scanner 100 is focused downward toward the eye 43 through the center of the light source 104 by virtue of being positioned directly above the light source 104 or through the shared optics 50 as described above. Likewise, an objective 108 of the camera 102 is aimed directly downward at the eye 43 through the center of light source 104. The camera 102 thus provides an image of the eye, viewed from above, to capture and evaluate the reflections off the eye 43 from the individual LEDs in the light source 104. This captures the topography of the cornea and provides a steep axis measurement of more conical corneas. An optimal distance from the camera objective 108 to the cornea that maximizes the contrast of the reflection of the light source 104 may be pre-determined by a theoretical analysis of the optical system, or through simulation.

The primary benefit of distance optimization is in accurate determination of the corneal astigmatic power and axis. A significant source of error in corneal astigmatic measurements is the knowledge of the location of the cornea relative to the machine. An exact knowledge of the location of the cornea affects the subsequent calculation, in addition to a precise focus of the reflection of the light source 104. In this regard, establishing an accurate distance from the camera objective 108 to the cornea is a primary concern, while maximizing focus is secondary. Furthermore, adjustment of the distance between the eye and the objective may be done by moving the chair or the objective relative to one another, as mentioned above. Likewise, the OCT may be used just to measure the distance, without the need to move anything else.

Figure 7:
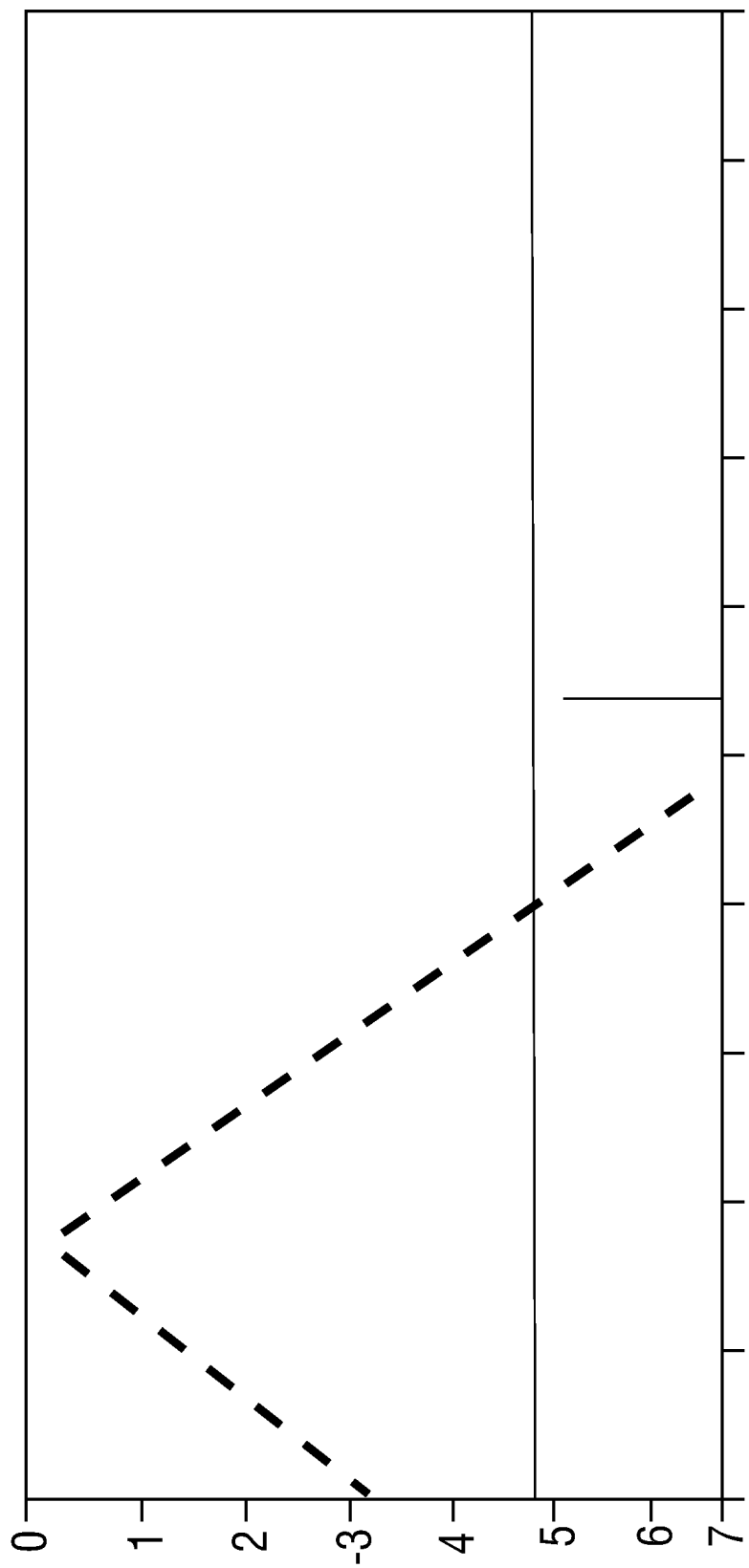
FIG. 7 is a graph of set of 2000 A-scans taken at 1000 Hz by an OCT scanner when measuring the initial distance from a camera objective to the eye.

An exemplary technique for automatically positioning the patient to focus the reflections of the light source LEDs on the camera objective 108 comprises a closed-loop iteration using the OCT as a position sensor to drive the vertical motion of the movable patient support 106, or chair. First, a set of 2000 A-scans taken at 1000 Hz measures the initial distance from the objective to the eye. The focus of the OCT 100 is always placed as close as possible to the zero "Optical Path Distance." The "Optical Path Distance" is changed with the Zed encoder to control the window of space imaged by the OCT. The "Optical Path Distance" is continuously swept through a range of 20 mm, so that every A-scan images a progressively deeper area than the previous. A stationary object, such as the cornea of the eye 43 will look like an inclined line using this Zed movement. Because the OCT images are the addition of the real and imaginary components of the spectrum, they display an addition of what is below the zero "Optical Path Length" and above it, making the stationary object look like an inverted "V", as indicated in FIG. 7, which is easily detectable. The vertex of the inverted "V" is located in the A-scan acquired when the zero "Optical Path Length" was at the eye surface. This method produces a very accurate measurement of the eye distance to the objective 108 of the camera 102, whose position is fixed and known with respect to the OCT scanner lens.

In a preferred embodiment, the physician presses and maintains pressed a control, such as a button on the joystick control 38, to start the OCT controlled chair motion. The next step is to move the chair 106 consistent with the detected position. Since the chair speed depends on the patient's weight and has a system-to-system variability, the final location may be slightly off from the target. In this case a second iteration of the process above described is implemented. For the second and subsequent iteration (in case they were needed) only 1000 A-scans are used. Shorter OCT time is justified because there is now a better estimate of the location of the eye 43. Preferably, the iterative algorithm works only while the doctor is pressing the control, and if the doctor stops pressing that control, the chair motion stops. The chair 106 also stops when it gets to the pre-determined optimal location where the reflection of the LEDs is focused or has the greatest sharpness, even if the control button is still pressed. During this process force sensors (not shown) in the objective 108 are closely monitored for contact of the patient with the objective, in which case the chair is backed away from the objective and the iteration is stopped. Once the eye is measured by the OCT to be within a tolerance from the pre-determined target location, the physician gets a visual that she/he can proceed to perform the function whose outcome depends on a proper positioning between the eye 43 and the objective 108.

Figure 8C:
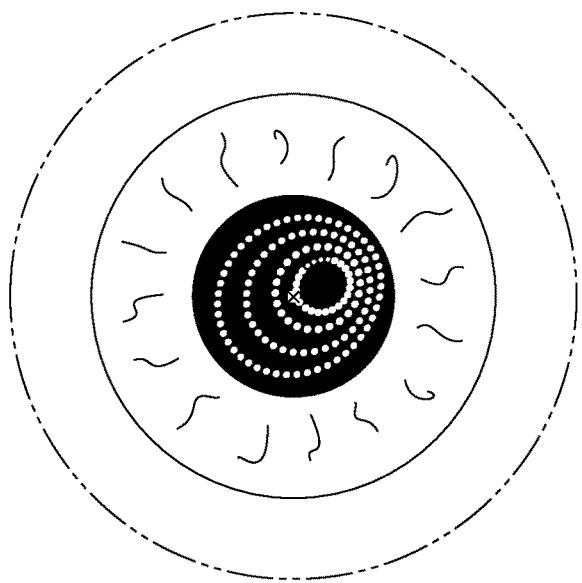
FIGS. 8A, 8B, and 8C are different views of the reflected light from the eye seen by a camera within the diagnostic and interventional system of the present application.
Figure 8B:
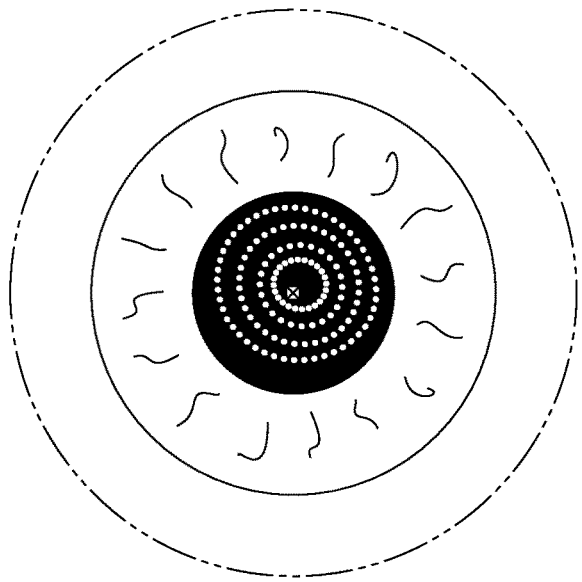
Figure 8A:
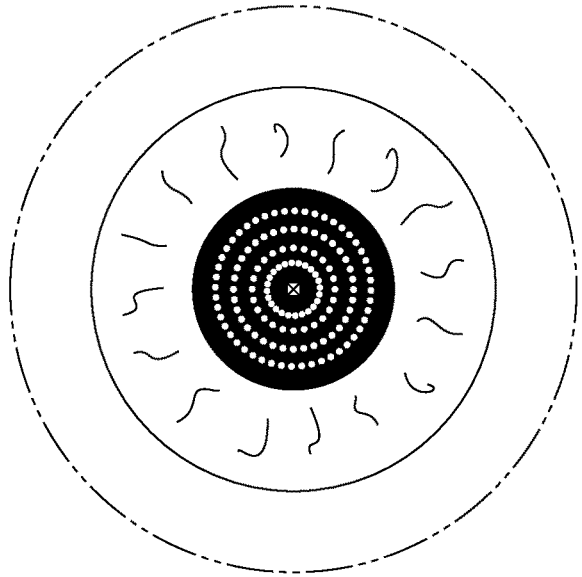

That is, the system measures the astigmatic axis, measures the power or curvature of the cornea, or performs some other such function. For example, the camera 102 captures an image of the reflection from the light source 104 off the eye 43. The image can then be viewed on the control panel 56 for direct evaluation by the physician, and is internally stored for use by the control electronics 54 such as when controlling the action of the cutting laser subsystem 44. FIGS. 8A, 8B, and 8C are different views of the reflected light from the light source 104 off the eye 43 as seen by the camera 102 within the diagnostic and interventional system 4. The images show 4 concentric rings of dots, or LED point reflections, though more or less rings may be used. A preferred embodiment is between 2-4 rings. FIG. 8A illustrates a relatively even, concentric pattern of circles reflected back from the circular arrays of LEDs, indicating little or no astigmatism. FIG. 8B shows a pattern of reflected LED dots that is slightly offset from a central axis and oval, indicating slight stigmatism. Finally, FIG. 8C shows a pattern which is highly irregular and offset from a central axis, indicating severe astigmatism. In each case, the orientation of the axis of the astigmatism is determined from the pattern of reflected dots, and the result is stored in the memory 57 of the laser eye surgery system.

An alternative technique for automatically positioning the patient relative to the laser system is to compute a contrast metric from the part of the video image that contains the reflection of the LEDs. The patient support 106 is then moved away from the objective 108 a short distance and the contrast measured again. If the contrast improves, the system then continues to move the chair 106 in the same direction until the contrast gets worst, then backs up to the previous maximum contrast location. If, on the other hand, the contrast gets worst, then the system moves the chair 106 towards the objective 108 until the contrast decreases. Then back to the maximum contrast location. This process is analogous to the autofocus feature that some cameras have.

A third method, also used in some camera autofocusing mechanisms, is phase detection. A partial beam splitter picks off some light from the reflected image and directs it to a number of micro lens pairs. These lenses project to small, independent sensors. Their data can be compared, such as with cross-correlation. Since these pairs of sensors correspond to specific regions in the camera's 102 field of view, the direction in which to move into focus can be found directly. Although more involved, this allows for faster focus finding and positioning.

A fourth method utilizes a light field camera to measure the reflected image. These kinds of cameras can produce several images, each with a different focal plane, from a single measurement. They do this by measuring not only the position of incoming light rays, but also the angle from which they came, using a microlens array in front of the sensor. From this data, the plane in which the dots are in focus can be calculated, yielding the current distance of the dots from the camera sensor. This distance can then be used to tell the chair to move directly in the correct direction. Similar to phase detection, this method also allows for direction movement from the data, in addition to looser tolerance of initial positioning, but at the cost of greater computational complexity and computation time.

All of these methods can be used in applications where iris registration is required as well (e.g. the VISX excimer laser). Instead of converging towards a reflection of dots on the cornea, the feedback of information would drive the patient chair to bring the iris plane into sharpest focus.

The use of the terms "a" and "an" and "the" and similar referents in the context of describing the invention (especially in the context of the following claims) are to be construed to cover both the singular and the plural, unless otherwise indicated here or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values here are merely intended to serve as a shorthand method of referring individually to each separate value falling within the range, unless otherwise indicated herein, and each separate value is incorporated into the specification as if it were individually recited herein. All methods described here can be performed in any suitable order unless otherwise indicated here or otherwise clearly contradicted by context. The use of any and all examples, or exemplary language (e.g., "such as") provided herein, is intended merely to better illuminate embodiments of the invention, and does not pose a limitation on the scope of the invention unless otherwise claimed. No language in the specification should be construed as indicating any non-claimed element as essential to the practice of the invention.

While preferred illustrated embodiments of this disclosure have been shown and described in an exemplary form with a certain degree of particularity, those skilled in the art will understand that the embodiments are provided by way of example only, and that various variations can be made without departing from the spirit or scope of the invention. Thus, it is intended that this disclosure cover all modifications, alternative constructions, changes, substitutions, variations, as well as the combinations and arrangements of parts, structures, and steps that come within the spirit and scope of the invention as generally expressed by the following claims and their equivalents.

What is claimed is:

1. A method of positioning a patient with respect to a laser eye surgery system, comprising:
   positioning an eye of a patient on a support below a camera objective within a laser eye surgery system containing an optical coherence tomography (OCT) scanner which includes an OCT interferometer;
   after positioning the eye, sensing a distance between the camera objective and the eye using the OCT scanner by performing a closed-loop iteration using the OCT scanner to produce an output graph indicative of a location of the eye relative to the camera objective, including: scanning a portion of an imaging light in the eye and receiving a portion of the imaging light that has returned from the eye, using the interferometer to detect a location of the eye based on interference patterns between a reference portion of the imaging light and the portion of the imaging light that has returned from the eye, and determining the distance between the camera objective and the eye based on a location of the eye detected by the interferometer, wherein performing the closed-loop iteration using the OCT scanner is initiated automatically by pressing and maintaining pressed a control to start a controlled motion of a patient chair and stopping motion of the patient chair when either the control is no longer pressed or one or more force sensors located at the camera objective transmits a signal indicating possible contact of the camera objective with the eye;
   after sensing the distance, transmitting the sensed distance between the camera objective and the eye to control electronics of the laser eye surgery system;
   after sensing the distance, based on knowledge of the sensed distance between the camera objective and the eye which has been determined by using the OCT scanner and interferometer, adjusting the distance between the camera objective and the eye to an adjusted distance which is within a threshold tolerance of a pre-determined target distance, wherein the pre-determined target distance is a pre-determined optimal distance from the camera objective to the eye that maximizes a contrast of a reflection of light sources off the cornea of the eye; and
   after adjusting the distance, and while the distance between the camera objective and the eye is at the adjusted distance, measuring an astigmatic axis or a power or curvature of the cornea of the eye by capturing an image of a reflection of a circular array of light sources off the cornea of the eye.

2. The method of claim 1, wherein adjusting the distance between the camera objective and the eye includes:
   comparing the sensed distance with the pre-determined target distance; and
   repositioning the camera objective toward or away from the support until the sensed distance is within the threshold tolerance of the pre-determined target distance.

3. The method of claim 1, wherein adjusting the distance between the camera objective and the eye includes:
   comparing the sensed distance with the pre-determined target distance; and
   repositioning the support toward or away from the camera objective until the sensed distance is within the threshold tolerance of the pre-determined target distance.

4. The method of claim 1, wherein the closed-loop iteration comprises taking a set of 2000 A-scans at 1000 Hz to measure an initial distance from the camera objective to the eye, wherein a focus of the OCT scanner is placed as close as possible to a zero "Optical Path Distance" and the "Optical Path Distance" is continuously swept through a range of 20 mm to produce an inverted "V" on the output graph and a vertex of the inverted "V" identifies the location of the eye.

5. The method of claim 1, further including displacing the eye toward or away from the camera objective based on a location of the eye determined from taking a set of 2000 A-scans, and then taking a set of 1000 A-scans to refine the location of the eye.

6. A method of positioning a patient with respect to a laser eye surgery system, comprising:

positioning an eye of a patient on a support below a camera objective within a laser eye surgery system containing an optical coherence tomography (OCT) scanner which includes an OCT interferometer;

after positioning the eye, sensing a distance between the camera objective and the eye using the OCT scanner by performing a closed-loop iteration using the OCT scanner to produce an output graph indicative of a location of the eye relative to the camera objective, including: scanning a portion of an imaging light in the eye and receiving a portion of the imaging light that has returned from the eye, using the interferometer to detect a position of the eye based on interference patterns between a reference portion of the imaging light and the portion of the imaging light that has returned from the eye, and determining the distance between the camera objective and the eye based on a location of the eye detected by the interferometer, wherein performing the closed-loop iteration using the OCT scanner is initiated automatically by pressing and maintaining pressed a control to start a controlled motion of a patient chair and stopping motion of the patient chair when either the control is no longer pressed or one or more force sensors located at the camera objective transmits a signal indicating possible contact of the camera objective with the eye;

comparing the sensed distance between the camera objective and the eye which has been determined by using the OCT scanner the and interferometer with a pre-determined target distance, wherein the pre-determined target distance is a pre-determined optimal distance from the camera objective to the eye that maximizes a contrast of a reflection of light sources off the cornea of the eye;

thereafter, adjusting a position between the support and the camera objective and sensing the distance again using the OCT scanner and the interferometer, until the support and the camera objective are located at adjusted relative positions where the sensed distance which has been determined by using the OCT scanner and the interferometer is within a threshold tolerance of the pre-determined target distance, and wherein adjusting the position is performed without capturing any images of the reflection of the light sources; and after adjusting the position, and while the support and the camera objective are located at the adjusted relative positions, measuring an astigmatic axis or a power or curvature of the cornea of the eye by capturing an image of a reflection of a circular array of light sources off the cornea of the eye.

7. The method of claim 6, wherein the closed-loop iteration comprises taking a set of 2000 A-scans at 1000 Hz to measure an initial distance from the camera objective to the eye, wherein a focus of the OCT scanner is placed as close as possible to a zero "Optical Path Distance" and the "Optical Path Distance" is continuously swept through a range of 20 mm to produce an inverted "V" on the output graph and a vertex of the inverted "V" identifies the location of the eye.

8. The method of claim 6, further including displacing the eye toward or away from the camera objective based on the location of the eye determined from taking a set of 2000 A-scans, and then taking a set of 1000 A-scans to refine the location of the eye.

* * * * *